US011511135B2

(12) United States Patent
Debatty et al.

(10) Patent No.: US 11,511,135 B2
(45) Date of Patent: Nov. 29, 2022

(54) RADIOTHERAPY APPARATUS COMPRISING AN IMAGING RING

(71) Applicant: ION BEAM APPLICATIONS, Louvain-la-Neuve (BE)

(72) Inventors: Alexandre Debatty, Hévillers (BE); Frédéric Dessy, Binche (BE); Yves Claereboudt, Nil-Saint-Vincent (BE)

(73) Assignee: Ion Beam Applications, Louvain-la-Neuve (BE)

( * ) Notice: Subject to any disclaimer, the term of this patent is extended or adjusted under 35 U.S.C. 154(b) by 0 days.

(21) Appl. No.: 17/773,238

(22) PCT Filed: Oct. 29, 2020

(86) PCT No.: PCT/EP2020/080467
§ 371 (c)(1),
(2) Date: Apr. 29, 2022

(87) PCT Pub. No.: WO2021/084045
PCT Pub. Date: May 6, 2021

(65) Prior Publication Data
US 2022/0347494 A1 Nov. 3, 2022

(30) Foreign Application Priority Data

Oct. 30, 2019 (EP) .................................... 19206319

(51) Int. Cl.
A61B 6/00 (2006.01)
A61N 5/10 (2006.01)
A61B 6/03 (2006.01)

(52) U.S. Cl.
CPC ............ *A61N 5/1082* (2013.01); *A61B 6/035* (2013.01); *A61B 6/4014* (2013.01); *A61B 6/4452* (2013.01)

(58) Field of Classification Search
CPC .... A61N 5/1082; A61B 6/035; A61B 6/4014; A61B 6/4452
See application file for complete search history.

(56) References Cited

U.S. PATENT DOCUMENTS

| 4,741,015 A | 4/1988 | Charrier |
| 2004/0005027 A1 | 1/2004 | Nafstadius |
| (Continued) | | |

FOREIGN PATENT DOCUMENTS

WO WO 00/74779 A1 12/2000

OTHER PUBLICATIONS

International Search Report for International Application No. PCT/EP2020/080467 dated Jan. 19, 2021 (3 pages).

*Primary Examiner* — Dani Fox
(74) *Attorney, Agent, or Firm* — Finnegan, Henderson, Farabow, Garrett & Dunner, LLP (57) ABSTRACT

A radiotherapy apparatus for the delivery of an energetic beam to a target tissue in a treatment zone, including: a rotatable gantry for rotating the end of a beam delivery system about a circle centered on an isocentre and normal to an axis of rotation Z1 of the gantry, the path between the end of the beam delivery system and the isocentre defining a central beam axis Z2 at every rotation angle of the gantry about the axis of rotation Z1; an imaging ring having a central bore and an imaging system for acquiring images of a patient in an imaging zone of the imaging system, wherein the imaging ring is located in the radiotherapy apparatus such that its imaging zone intersects the axis of rotation Z1 of the gantry, and wherein the imaging ring is mechanically coupled to the rotatable gantry through a mechanical structure.

14 Claims, 5 Drawing Sheets

(56) References Cited

U.S. PATENT DOCUMENTS

| | | |
|---|---|---|
| 2004/0184579 A1 | 9/2004 | Mihara et al. |
| 2008/0219407 A1 | 9/2008 | Kaiser et al. |
| 2009/0065717 A1 | 3/2009 | Kaiser et al. |
| 2011/0085640 A1* | 4/2011 | Fadler .................. A61B 6/4441 378/65 |
| 2011/0301449 A1 | 12/2011 | Maurer, Jr. |
| 2012/0307973 A1 | 12/2012 | Dirauf et al. |
| 2013/0256551 A1 | 10/2013 | Yao et al. |

* cited by examiner

RADIOTHERAPY APPARATUS COMPRISING AN IMAGING RING

This application is a U.S. National Stage Application of International Application No. PCT/EP2020/080467, filed Oct. 29, 2020, which application claims priority from European Application 19206319.6, filed on Oct. 30, 2019. The entire contents of the aforementioned applications are incorporated herein by reference.

FIELD OF THE INVENTION

The present invention relates to a radiotherapy apparatus comprising a rotatable gantry and having imaging capabilities.

DESCRIPTION OF PRIOR ART

In a gantry-based radiotherapy apparatus, a gantry moves around the patient such to rotate the end of the beam transport system about a circle centered on an isocentre and normal to an axis of rotation Z, which is generally horizontal. The path between the end of the therapeutic beam transport system and the isocentre defines a central beam axis at every angle around the axis of rotation Z. A target tissue to be treated by a therapeutic beam, such as a tumor, is generally positioned near the isocentre. This is advantageous in that, for any angular position of the gantry, the target tissue can be irradiated by minor deflections of the therapeutic beam with respect to the central beam axis, thanks to appropriate technical means, such as scanning magnets in the case of a particle therapy apparatus.

In such a radiotherapy apparatus, the patient can lie on a couch or any other support, usually intersecting the gantry axis of rotation Z. Depending on the specificities of the treatment to be received by the patient, the couch or any other support for the patient, and ultimately the patient body, can have different orientations with respect to the gantry axis of rotation Z. In coplanar radiotherapy, the patient is supine and his body is aligned with the gantry axis of rotation Z. In non-coplanar radiotherapy, the longitudinal axis of the patient's body is not coaxial with the gantry axis of rotation Z.

Associated with a radiotherapy system is an imaging system to provide in-treatment images that are used to set up and, in some examples, guide the radiation delivery procedure and track in-treatment target motion. Different systems and imaging techniques can be used for such purpose.

In one configuration of the prior art, imaging devices, such as x-ray tubes and panels, can be rigidly mounted to the gantry, or alternatively coupled to the gantry in that they can independently be rotated relative to the gantry about an axis of rotation coaxial with the gantry axis of rotation, such as disclosed in document US20110085640A1. These arrangements however only allow to perform in-treatment imaging at a substantially coplanar configuration of the gantry and patient support because the imaging devices do not have the necesseray mechanical degrees of freedom for properly imaging a patient's body whose longitudinal axis is not coaxial with the gantry axis of rotation Z. For properly imaging a supine patient, it is indeed in general necessary that the imaging devices can be rotated about an axis of rotation coaxial with the patient's body longitudinal axis.

Other in-treatment imaging systems include independent (robotized) articulated systems for moving imaging sources and detectors. Such systems can be totally independent or coupled to a patient positioning system. Their motion is however quite complex to control and they are usually not well suited for imaging the patient at the isocenter. As such independent articulated systems move in their own frame of reference, it is also necessary to transform the image coordinates in the radiotherapy apparatus frame of reference. Furthermore, the multiplicity of the moving elements such systems usually comprise induces a risk of collision with the gantry or with the patient, which is not satisfactory for obvious safety reasons. Such a robotized articulated system is for example described in document US 2009/0074151.

Document EP 2 539 020 discloses systems for image-guided radiation treatment (IGRT). The systems described rely on the presence of several beam members extending between first and second ends of the rotatable gantry. A radiation treatment head is movably mounted on one of these beam members for achieving non-coplanar radiotherapy, while imaging sources and detectors are mounted on two others of these beam members. Such arrangements are quite cumbersome, with the different beam members forming a cage-like structure around the patient. Furthermore, the arrangements described in this document cannot be applied to every radiotherapy technique. Indeed, a movable treatment head mounted to the gantry is for example not realistically achievable with a particle beam apparatus wherein the beam transport and delivery system rely on complex and heavy equipments rigidly coupled to the gantry.

Document US 2013/0158382 discloses a medical treatment system with non-coplanar capability. In particular, the system comprises a treatment ring comprising at least one treatment head. The system may further include an imaging device, which can be positioned in front of a beam stopper or in place of it. The treatment ring is connected to a rotating member, equivalent to a rotatable gantry, and can be angularly displaced from the rotating member by a tilt angle at a pivot point. The pivot point may be a pin, hinge or any other mechanism facilitating the tilting of treatment ring in relation to the rotating member. The treatment ring can furthermore be rotated about its own axis, with treatment devices fixed to particular circumferential locations. Alternatively, the treatement ring does not rotate about its own axis, but instead, treatment devices rotate about the axis of treatment ring with respect to treatment ring. This rotation may be accomplished for example by treatment devices moving along circumferential tracks within treatment ring. The arrangements described in this prior art document rely on the presence of a tilt angle between the treatment ring and the gantry for delivering non-coplanar treatment, rather than on a change of the patient couch orientation with respect to the gantry axis of rotation. The arrangements described in this document cannot be applied to every radiotherapy technique. Indeed, such tilt angle between a treatment ring comprising the treatment head and a gantry is for example not realistically achievable with a particle beam apparatus wherein the beam transport and delivery system rely on complex and heavy equipments rigidly coupled to the gantry.

Document U.S. Pat. No. 4,741,015 discloses an apparatus for beaming in a multiplicity of directions around the body of a horizontally disposed stationary patient so that a complete, three-dimensional or sectional picture of the patient's anatomy is made available. No treatment beam is provided in said document.

Document US 2004/0005027 discloses a structure comprising a C-shaped jaw portion rotatably supported through a rotation connection. A ring portion is rotatably attached to the C-shaped jaw portion through rotatable supports.

Document WO 00/74779 discloses an irradiation device comprising an outer gantry part and an inner gantry part, the inner gantry part being rotatably supported by the outer gantry part at two support locations. No imaging means are described.

US 2004/0184579 discloses embodiments of a radiation treatment apparatus where an imaging ring is rotatable about a horizontal or vertical axis.

US 2012/0307973 discloses a radiotherapy system having a radiation source provided in a projecting arm immovably secured to a sidewall of a treatment room. No rotatable gantry is provided in this document.

US 2013/0256551 discloses a radiation therapy apparatus wherein an imaging system is configured to be rotationally slidable against an arc-shaped sub-rail and is mounted on a proximal side gantry, rotatable about a horizontal axis.

SUMMARY OF THE INVENTION

It is an object of the present invention to provide a radiotherapy apparatus having a beam delivery system mounted to a rotatable isocentric gantry and comprising an imaging system which can provide images of a target tissue located at the isocenter. The imaging system of the radiotherapy apparatus should be able to provide images at the isocenter for any angular position of the gantry by directing an imaging beam along a broader range of directions, including directions for imaging a patient's body whose longitudinal axis is not coaxial with the gantry axis of rotation, directions departing from a plane perpendicular to the gantry axis and directions near or coaxial to a beam axis, notwithstanding the presence of a beam delivery system. The radiotherapy apparatus must also be reliable and safe for the patient and medical staff.

The present invention is defined in the appended independent claim. Preferred embodiments are defined in the dependent claims.

In particular, the invention concerns a radiotherapy apparatus for the delivery of an energetic beam to a target tissue in a treatment zone of said radiotherapy system, wherein
a) the radiotherapy apparatus comprises a rotatable gantry for rotating the end of a beam delivery system about a circle centered on an isocentre I and normal to an axis of rotation Z1 of the gantry, the path between the end of the beam delivery system and the isocentre I defining a central beam axis Z2 at every rotation angle of the gantry about the axis of rotation Z1;
b) the radiotherapy apparatus comprises an imaging ring, said imaging ring comprising a central bore and being defined by a bore axis X1 extending along said central bore, and by a first and a second transverse axis X2, X3 defining an imaging ring plane (X2, X3), said axes X1, X2, X3 being orthogonal and intersecting at a center R of said imaging ring, said imaging ring comprising:
  i. an imaging system for acquiring images of a patient in an imaging zone of said imaging system, said imaging zone intersecting the bore axis X1;
  ii. a beamline portion with a channel for the passage of the energetic beam through the imaging ring;
c) the imaging ring is located in the radiotherapy apparatus such that its imaging zone intersects the axis of rotation Z1 of the gantry, and the imaging ring is mechanically coupled to the rotatable gantry through a mechanical structure, wherein:
  i. the mechanical structure is mechanically coupled to the gantry in that said mechanical structure is rotatable with respect to the gantry about the central beam axis Z2, and
  ii. the imaging ring is mechanically coupled to the mechanical structure in that:
    the imaging ring center R is located on the central beam axis Z2 and;
    the imaging ring is rotatable with respect to the mechanical structure about a second axis of rotation Y2 of the imaging ring, said axis of rotation Y2 belonging to the the imaging ring plane (X2, X3), said axis of rotation Y2 being perpendicular to said central beam axis Z2.

The mechanical structure may be mechanically coupled to the gantry in such a way that the path between the end of the beam delivery system and the isocentre is not impeded by the mechanical structure.

In an advantagesous embodiment, the imaging ring is mechanically coupled to the mechanical structure in that the second axis of rotation Y2 is perpendicular to the central beam axis Z2, and the channel 51 for the passage of the energetic beam irradiating said target tissue is located on an axis perpendicular to the second axis of rotation Y2.

In an advantageous embodiment, the imaging ring center R is located at the isocenter I.

In an advantageous embodiment, the imaging system comprises several movable imaging devices movably mounted to the imaging ring in that they can be translated and/or rotated with respect to the imaging ring along a circular path about the center R of the imaging ring.

In an advantageous embodiment, the imaging system comprises two movable X-ray generators, such as X-ray tubes, and two movable X-ray detectors, such as flat panel detectors.

In an advantageous embodiment, the movable imaging devices are enclosed within an outer shell of the imaging ring.

In an advantageous embodiment, beam measuring devices are provided in the beamline portion of the imaging ring across the channel for the passage of the energetic beam.

In an advantageous embodiment, the radiotherapy system is a particle beam apparatus and the end of the beam delivery system corresponds to the outlet of a particle beam nozzle.

In an advantageous embodiment, the outer surface of the beamline portion of the imaging ring comprises a recess for receiving the particle beam nozzle.

In an advantageous embodiment, the beam measuring devices are provided in said recess.

In an advantageous embodiment, the mechanical structure comprises two arms forming a plane with the central beam axis Z2 and being rigidly coupled to a central portion of said mechanical structure, said central portion being mechanically coupled to the gantry in that the mechanical structure is rotatable with respect to the gantry about the central beam axis Z2, said central portion surrounding the end of the beam delivery system, the second axis of rotation Y2 intersecting the ends of said two arms.

In an advantageous embodiment, the imaging ring is mechanically coupled to the ground or to a second coupling point on the gantry.

In an advantageous embodiment, the radiotherapy apparatus comprises a patient positioning system comprising a patient support, such as a couch, said patient positioning system comprising a controller for synchronizing the motion of the patient support with the motion of the gantry and of the imaging ring.

In an advantageous embodiment, the patient positioning system is mechanically coupled to the imaging ring.

BRIEF DESCRIPTION OF THE DRAWINGS

These and further aspects of the invention will be explained in greater detail by way of example and with reference to the accompanying drawings in which.

The figures are not drawn to scale.

DETAILED DESCRIPTION OF PREFERRED EMBODIMENTS

Figure 1:
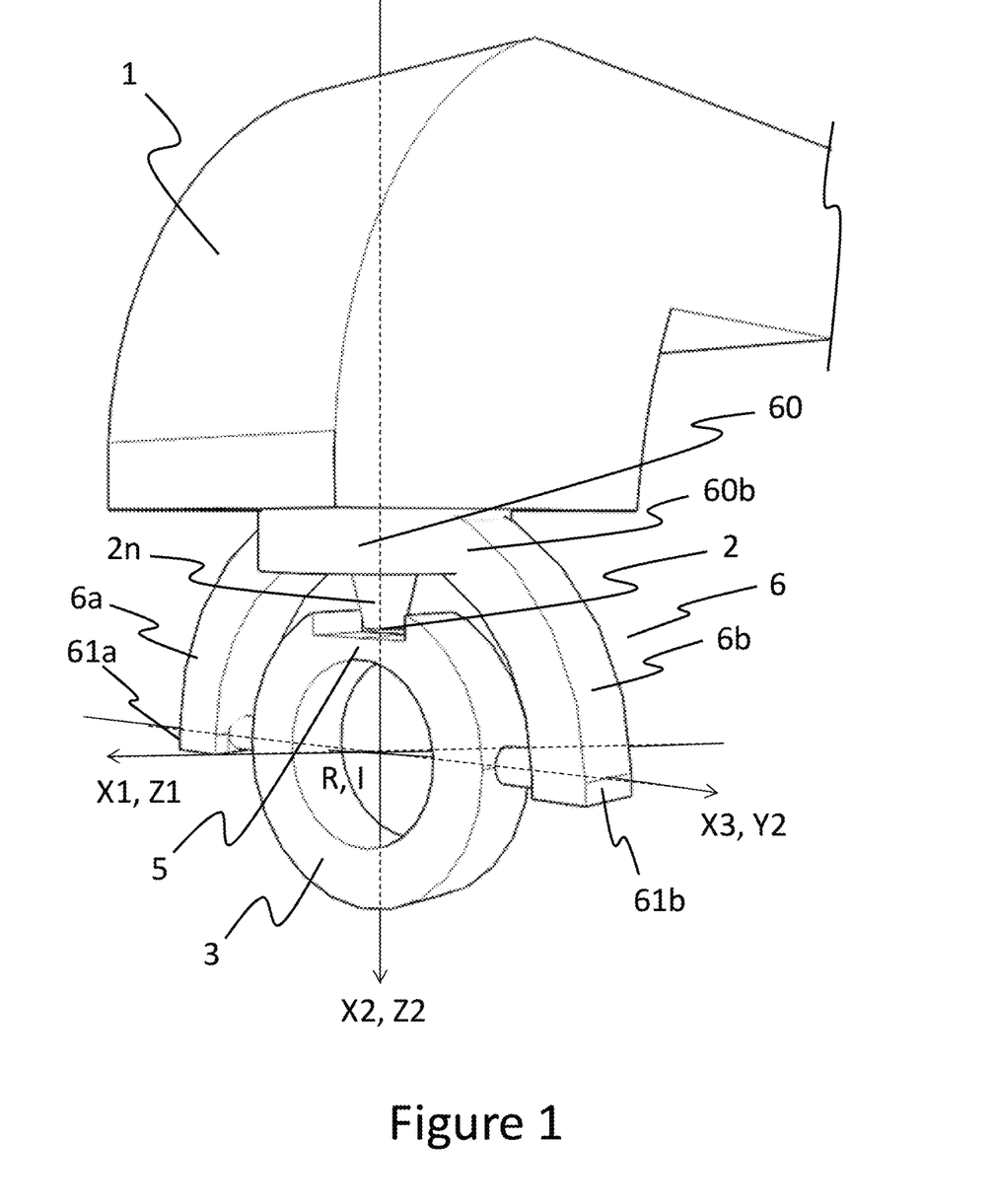
FIG. 1 is a view of a radiotherapy apparatus according to the present invention in a coplanar configuration.
Figure 2:
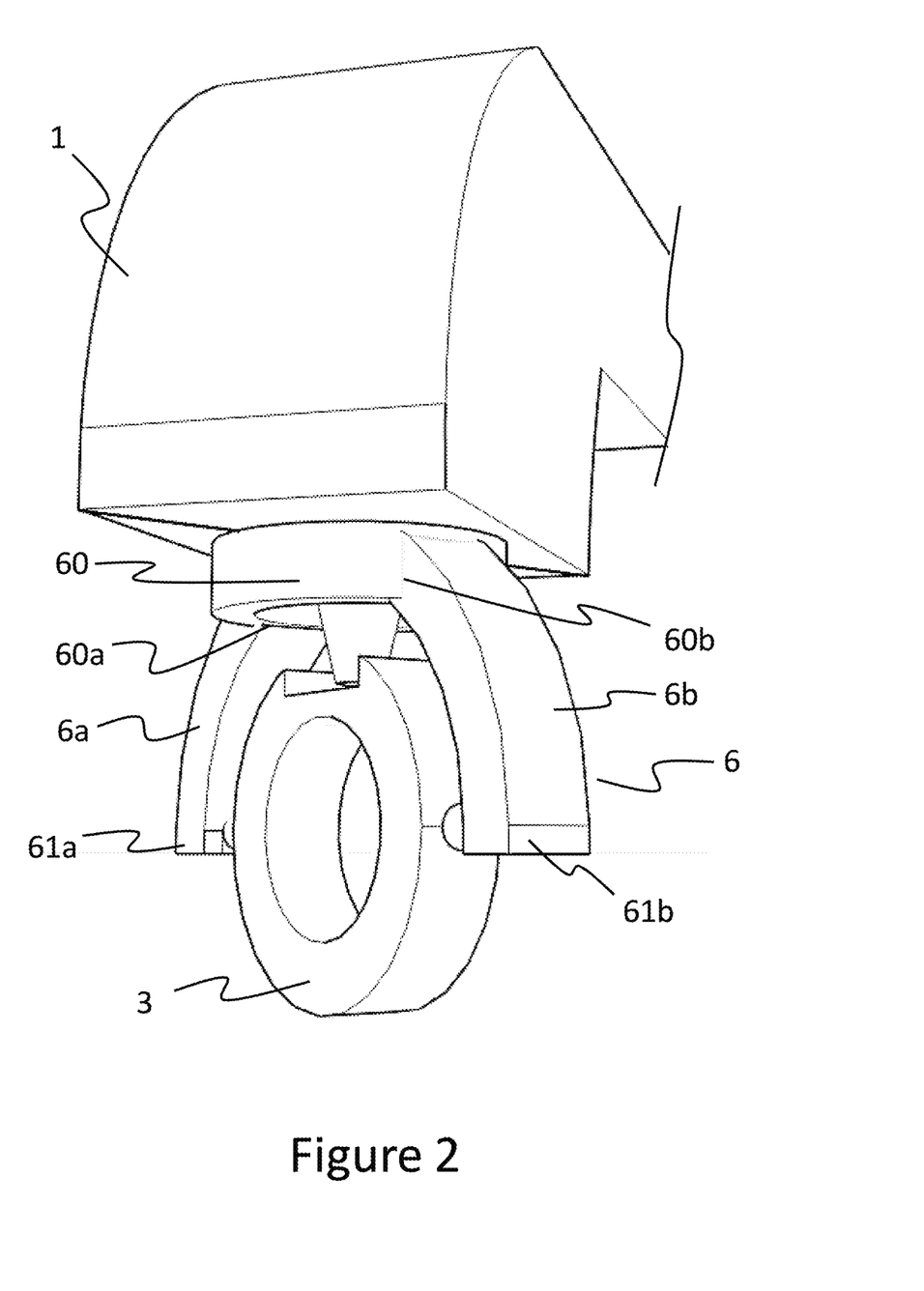
FIG. 2 is a view of a radiotherapy apparatus according to the present invention in a non-coplanar configuration.
Figure 3:
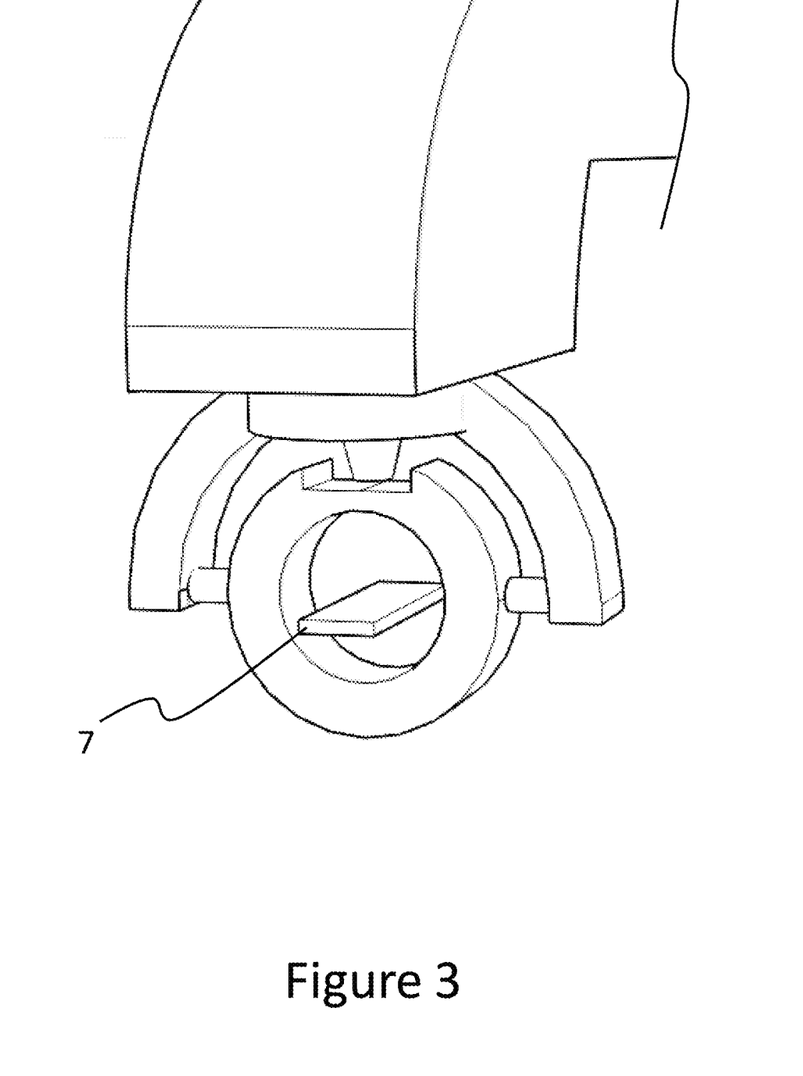
FIG. 3 is a view of a radiotherapy apparatus according to the present invention where the patient support is schematically represented.
Figure 4:
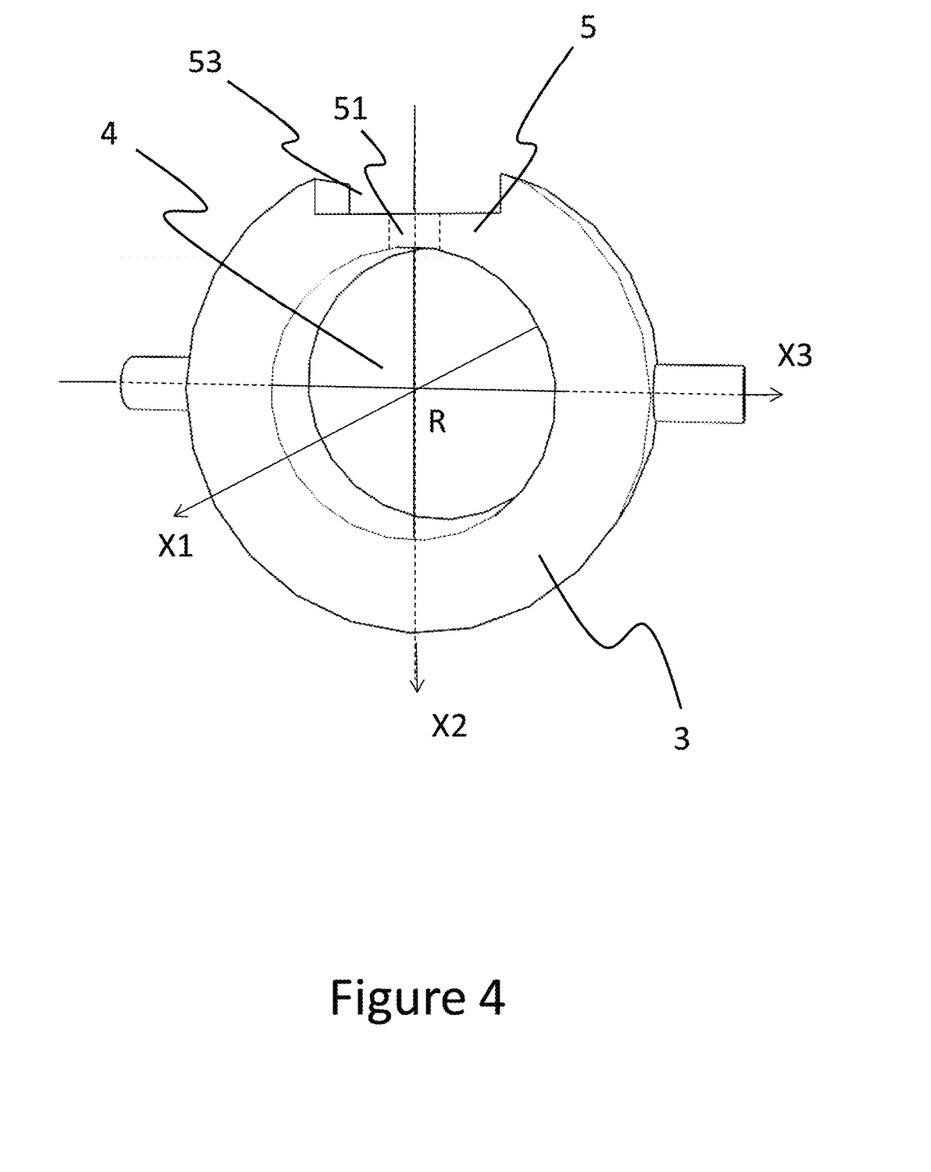
FIG. 4 is a view of an imaging ring from a radiotherapy apparatus according to the present invention.

FIGS. 1 and 2 illustrate an example of a radiotherapy apparatus according to the present invention, for the delivery of an energetic beam to a target tissue in a treatment zone of said radiotherapy system.

The radiotherapy apparatus comprises a rotatable gantry 1 for rotating the end 2 of a beam delivery system about a circle centered on an isocentre I and normal to an axis of rotation Z1 of the gantry 1. The path between the end 2 of the beam delivery system and the isocentre I defines a central beam axis Z2 at every rotation angle of the gantry 1 about the axis of rotation Z1. As represented in FIG. 1, the end 2 of the beam delivery system can be the tip of a nozzle 2*n* mounted on the rotatable gantry 1.

One essential feature of the radiotherapy apparatus is an imaging ring 3. The imaging ring comprises a central bore 4. The imaging ring 3 is defined by a bore axis X1 extending along said central bore 4 and by a first and a second transverse axis X2, X3 defining an imaging ring plane (X2, X3). The axes X1, X2, X3 are orthogonal and intersect at a center R of said imaging ring 3. The imaging ring 3 comprises:
 i. an imaging system for acquiring images of a patient in an imaging zone of said imaging system, wherein the imaging zone intersects the bore axis X1;
 ii. a beamline portion 5 with a channel 51 for the passage of the energetic beam through the imaging ring 3;

The imaging ring 3 is located in the radiotherapy apparatus such that its imaging zone intersects the axis of rotation Z1 of the gantry, and the imaging ring 3 is mechanically coupled to the rotatable gantry 1 through a mechanical structure 6, wherein:
 i. the mechanical structure 6 is mechanically coupled to the gantry 1 in that said mechanical structure 6 is rotatable with respect to the gantry 1 about the central beam axis Z2, and
 ii. the imaging ring 3 is mechanically coupled to the mechanical structure 6 in that:
  1. the imaging ring 3 center R is located on the central beam axis Z2 and;
  2. the imaging ring 3 is rotatable with respect to the mechanical structure 6 about a second axis of rotation Y2 of the imaging ring 3, said axis of rotation Y2 belonging to the the imaging ring plane (X2, X3) said axis of rotation Y2 being perpendicular to the central beam axis Z2.

The mounting of the imaging system on the imaging ring 3 offers a very advantageous mechanical configuration. As the imaging ring 3 is rotatable about the central beam axis Z2 and second axis of rotation Y2 relative to the gantry 1, advantageously thanks to mechanical actuators and a dedicated control system, the imaging system can thus be used to acquire images at the isocenter for any angular position of the gantry and for both coplanar and non coplanar configurations of the patient with respect to the axis of rotation of the gantry. The imaging ring 3 can indeed be rotated around the two axes of rotation Z2, Y2 such that the ring bore axis X1 is coaxial with the patient support longitudinal axis, even for non coplanar configurations of the patient support thus and for any angular position of the gantry 1.

Compared to the prior art technologies wherein independent articulated imaging system mechanical supports are moved relative to a fixed frame of reference corresponding the floor of the room where the radiotherapy apparatus is located, the mechanical coupling of the imaging ring 3 to the rotatable gantry 1 allows to minimize the degrees of freedom that need to be dedicated to the imaging ring 3. Indeed, the two degrees of freedom in rotation, with respect to axes Z2, Y2, together with the presence of a beamline portion 5 with a channel 51 for the passage of the energetic beam through the imaging ring 3, are sufficient to guarantee a proper positioning of the the imaging system for any angular position of the gantry and for any coplanar and non coplanar configuration of the radiotherapy apparatus. The beamline channel 51 can comprise vacuum maintaining elements and/or materials transmitting almost all of the energetic beam. The mechanical structure 6 is thus mechanically coupled to the gantry 1. The mechanical coupling between the mechanical structure 6 and the gantry 1 can result from a direct mechanical coupling between the mechanical structure 6 and the gantry 1, or from a mechanical coupling between the mechanical structure 6 and an element rigidly coupled to the gantry 1, such as the beam nozzle 2*n*.

Furthermore, in this configuration, the imaging system mechanical support, i.e. the imaging ring 3, is displaced directly with respect to the frame of reference of the beam delivery system, i.e. the rotatable gantry. Having the same frame of reference for the beam delivery system and the imaging system reduces therefore the complexity to tackle for imaging a target tissue positioned at the isocenter of the gantry. In this configuration with a common frame of reference, it is indeed not necessary to provide an additional positioning system to the imaging system for measuring its relative position with respect to the gantry.

In this configuration, the imaging ring 3 is preferably mechanically coupled to the mechanical structure 6 in that the second axis of rotation Y2 is perpendicular to the the central beam axis Z2. The channel 51 for the passage of the energetic beam irradiating said target tissue is located on an axis perpendicular to the second axis of rotation Y2. In this configuration, when the channel 51 is located on axis X2 of the imaging ring, the second axis of rotation Y2 is thus advantageously coaxial with second transverse axis X3 as represented in FIGS. 1 & 2.

In a preferred embodiment, as represented in FIGS. 1 & 2, the mechanical structure 6 and imaging ring 3 are configured such that the imaging ring center R is located on the isocenter I. In this configuration, the central beam axis Z2 and the second axis of rotation Y2 of the imaging ring 3 intersect at the isocenter I and this for any angular position of the gantry 1. In other words, the imaging ring center R has an invariant position under the rotation of the gantry 1 in a fixed frame of reference (attached to the floor). This is advantageous in that in this configuration, imaging at the isocenter I of the gantry is equivalent to imaging at the imaging ring center R for any angular position of the gantry 1.

Figure 5:
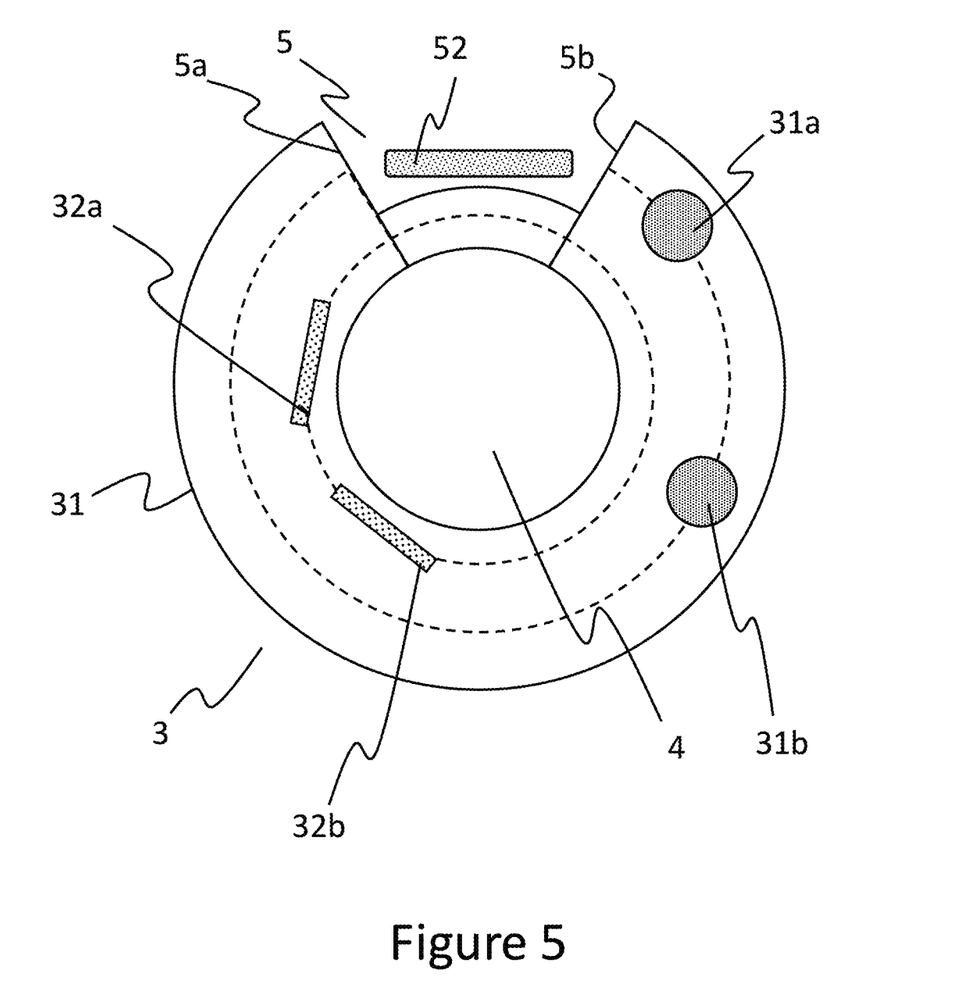
FIG. 5 is a schematic cross sectional view of an imaging ring from a radiotherapy apparatus according to the present invention.

As discussed supra, the imaging ring 3 comprises an imaging system for acquiring images of a patient in an imaging zone of said imaging system. Such imaging devices can be movably mounted to the imaging ring 3, advantageously in that they can be translated and/or rotated with respect to the imaging ring 3 along a circular path about the center R of the imaging ring 3. As represented in FIG. 5, such imaging devices can comprise two movable X-ray generators, such as X-ray tubes 31a, 31b, and two movable X-ray detectors, such as flat panel detectors 32a, 32b, configured to implement a cone beam computed tomography scanning technique (CBCT). In the embodiment represented in FIG. 5, the imaging ring 3 is configured such that the flat panel detectors 32a, 32b can move along a full circular path about the center R of the imaging ring 3, while the X-ray tubes 31a, 31b can move along a circular arc about the center R of the beamline portion 5 but only outside of the beamline portion 5 delimited by its two ends 5a, 5b. In other embodiments, the imaging system can comprise imaging devices configured to implement a classical computed tomography scanning technique (CT-scan). In other embodiments, the imaging ring 3 can comprise imaging devices for implementing other imaging techniques such as prompt gamma or positron-emission tomography (PET). In some embodiments, a single imaging ring 3 can comprise a plurality of imaging devices configured to implement different imaging techniques.

Referring to FIG. 5, the imaging ring 3 may be tilted enough for allowing the imaging ring to depart from the beam nozzle 2n. The imaging ring can then be rotated until a X-ray tube 21a or 31b appears in proximity to the beam nozzle. In this configuration, an image can be taken in a direction near to the central beam axis Z2.

When movable devices are mounted to the imaging ring 3, the imaging ring 3 advantageously comprises an outer shell 31 for enclosing said movable devices, such as represented in FIGS. 1-5. Such shell 31 increases the safety of the radiotherapy apparatus according to the invention for the patient, because it suppresses the risk of collision between the movable devices 31a, 31b, 32a, 32b and the patient.

The imaging ring 3 can also comprise at least one beam measuring device 52 provided in the beamline portion 5 across the channel 51 for the passage of the energetic beam, such as an ionization chamber, a flat panel or a range monitoring device. Such kinds of beam measuring device device can indeed be used to check the properties of the beam circulating through across the channel 51 before being delivered to the patient. Such measuring device is of course only operated when the energetic beam circulates across the channel 51, which occurs mostly in coplanar configuration of the radiotherapy apparatus for any angular position of the gantry 1. In non-coplanar configurations of the radiotherapy apparatus, the energetic beam will only circulate across the channel 51 at specific angular positions of the gantry 1, and the beam measuring device 52 can thus only be operated at such specific angular positions.

In the embodiment represented in FIGS. 1-5, the radiotherapy apparatus is configured to deliver a particle beam. In such an embodiment, the end of the beam delivery system advantageously corresponds to the outlet 2 of a particle beam nozzle 2n. In this configuration, the outer surface of the beamline portion 5 of the imaging ring 3 can comprise a recess 53 for receiving the particle beam nozzle 2n. Such recess allows to increase the length of the particle beam nozzle 2n and consequently to reduce the distance between the outlet 2 of the particle beam nozzle 2n and the isocenter I. This configuration is advantageous in that it minimizes the beam broadening observed in case of a large nozzle-to-isocenter distance. The beam measuring devices 52 is then advantageously provided in said recess 53. As represented in FIGS. 1-5, the gantry 1 is advantageously a cantilever gantry in the shape of a C-arm, on which the beam delivery system is mounted in a cantilevered manner such to be rotated about the axis of rotation Z1. In other embodiments, the gantry in the gantry can be in the shape of a toroid or ring, which has a central opening or bore to allow the patient's body to extend through. The beam delivery system is then rotatably mounted on the perimeter of the ring. In another embodiment, instead of a particle beam apparatus, the radiotherapy apparatus can be a conventional radiotherapy apparatus.

As represented in FIGS. 1 & 2, the mechanical structure can comprise two arms 6a, 6b forming a plane with the the central beam axis Z2 and each arm 6a, 6b having a first end 60a, 60b being rigidly coupled to a central portion 60 of the mechanical structure 6. The central portion 60 is mechanically coupled to the gantry 1 in that the mechanical structure 6 is rotatable with respect to the gantry 1 about the the central beam axis Z2. In this configuration, the particle beam nozzle 2n is advantageously inserted in a through hole of the central portion 60, such that the central portion surrounds the particle beam nozzle 2n. The imaging ring 3 is then coupled to the the second ends 61a, 61b of the two arms 6a, 6b, with the second axis of rotation Y2 of the imaging ring intersecting said second ends 61a, 61b.

In some embodiments, the imaging ring 3 can be mechanically coupled to the ground or to a second coupling point on the gantry 1, with the appropriate degrees of freedom for such mechanical coupling, in order to strengthen the whole mechanical structure.

The radiotherapy apparatus according to the invention advantageously comprises a patient positioning system comprising a patient support, such as a couch 7. Such patient positioning system is advantageously robotized and possesses the necessary mechanical degrees of freedom to position the patient with the target tissue at the isocenter I of the radiotherapy apparatus. The patient positioning system advantageously also comprises a controller for synchronizing the motion of the patient support with the motion of the gantry 1 and of the imaging ring 3, in order to avoid collisions between these different elements. In an advantageous embodiment, the patient positioning system is mechanically coupled to the imaging ring 3 with the appropriate degrees of freedom for such mechanical coupling, in that the synchronization of the imaging ring 3 and the patient positioning system is facilitated.

In the radiotherapy apparatus according to the invention, the collision risk for the patient is higly reduced and the gantry can turn much faster than any other gantry solution.

The invention claimed is:
1. A radiotherapy apparatus for the delivery of an energetic beam to a target tissue in a treatment zone
   comprising:
   a rotatable gantry for rotating the end of a beam delivery system about a circle centered on an isocentre and normal to an axis of rotation of the gantry, the path between the end of the beam delivery system and the isocentre defining a central beam axis at every rotation angle of the gantry about the axis of rotation;

an imaging ring, the imaging ring including a central bore and being defined by (1) a bore axis X1 extending along the central bore and (2) a first and a second transverse axis X2, X3 defining an imaging ring plane, the axes X1, X2, X3 being orthogonal and intersecting at a center of the imaging ring, wherein the imaging ring further includes:

an imaging system for acquiring images of a patient in an imaging zone of the imaging system, the imaging zone intersecting the bore axis X1, and a beamline portion with a channel for the passage of the energetic beam through the imaging ring;

wherein the imaging ring is located in the radiotherapy apparatus such that the imaging zone intersects the axis of rotation Z1 of the gantry, and the imaging ring is mechanically coupled to the rotatable gantry through a mechanical structure, wherein:

the mechanical structure is mechanically coupled to the gantry in that the mechanical structure is rotatable with respect to the gantry about the central beam axis Z2, and the imaging ring is mechanically coupled to the mechanical structure in that:

(1) the imaging ring center R is located on the central beam axis Z2 and, (2) the imaging ring is rotatable with respect to the mechanical structure about a second axis of rotation Y2 of the imaging ring, the axis of rotation Y2 belonging to the imaging ring plane, the axis of rotation Y2 being perpendicular to the central beam axis Z2.

2. The radiotherapy apparatus according to claim 1, wherein the imaging ring is mechanically coupled to the mechanical structure in that the second axis of rotation Y2 is perpendicular to the central beam axis Z2;

the channel for the passage of the energetic beam irradiating target tissue is located on an axis perpendicular to the second axis of rotation Y2.

3. The radiotherapy apparatus according to claim 2, wherein the imaging ring center is located at the isocenter.

4. The radiotherapy apparatus according to claim 1, wherein the imaging system comprises a plurality of movable imaging devices, each movably mounted to the imaging ring in that the devices are configured to be translated with respect to the imaging ring along a circular path about the center of the imaging ring.

5. The radiotherapy apparatus according to claim 4, wherein the moveable imaging devices comprise at least two movable X-ray generators and two movable X-ray detectors.

6. The radiotherapy apparatus according to claim 4, wherein the movable imaging devices are enclosed within an outer shell of the imaging ring.

7. The radiotherapy apparatus according to claim 1, wherein a plurality of beam measuring devices are provided in the beamline portion of the imaging ring across the channel for the passage of the energetic beam.

8. The radiotherapy apparatus according to claim 7, wherein the radiotherapy system is a particle beam apparatus and an output of the beam delivery system corresponds to a particle beam nozzle.

9. The radiotherapy apparatus according to claim 8, wherein an outer surface of the beamline portion of the imaging ring comprises a recess for receiving the particle beam nozzle.

10. The radiotherapy apparatus according to claim 9, wherein the beam measuring devices are provided in the recess.

11. The radiotherapy apparatus according to claim 1, wherein the mechanical structure comprises two arms forming a plane with the central beam axis Z2 and being rigidly coupled to a central portion of the mechanical structure, the central portion being mechanically coupled to the gantry in that the mechanical structure is rotatable with respect to the gantry about the central beam axis Z2, the central portion surrounding the end of the beam delivery system, the second axis of rotation Y2 intersecting the ends of the two arms.

12. The radiotherapy apparatus according to claim 1, wherein the imaging ring is mechanically coupled to a second coupling point on the gantry.

13. The radiotherapy apparatus according to claim 1, wherein the apparatus further includes a patient positioning system comprising a patient support that further includes a controller for synchronizing motion of the patient support with motion of both the gantry and of the imaging ring.

14. The radiotherapy apparatus according to claim 13, wherein the patient positioning system is mechanically coupled to the imaging ring.

* * * * *